United States Patent
Kurata et al.

(10) Patent No.: US 11,313,803 B2
(45) Date of Patent: Apr. 26, 2022

(54) OH RADICAL MEASUREMENT DEVICE AND METHOD USING AN OH RADICAL DETECTION PROBE

(71) Applicant: IHI CORPORATION, Tokyo (JP)

(72) Inventors: Takao Kurata, Tokyo (JP); Katsumi Takahashi, Tokyo (JP); Kazuyuki Sakamoto, Tokyo (JP)

(73) Assignee: IHI CORPORATION, Tokyo (JP)

( * ) Notice: Subject to any disclaimer, the term of this patent is extended or adjusted under 35 U.S.C. 154(b) by 237 days.

(21) Appl. No.: 16/545,342

(22) Filed: Aug. 20, 2019

(65) Prior Publication Data

US 2019/0376903 A1 Dec. 12, 2019

Related U.S. Application Data

(63) Continuation of application No. PCT/JP2018/004931, filed on Feb. 13, 2018.

(30) Foreign Application Priority Data

Feb. 23, 2017 (JP) .............................. JP2017-032024

(51) Int. Cl.
*G01N 21/77* (2006.01)
*G01N 21/78* (2006.01)
*G01N 33/00* (2006.01)
*G01N 30/72* (2006.01)
*G01N 30/02* (2006.01)

(52) U.S. Cl.
CPC ......... *G01N 21/77* (2013.01); *G01N 33/0013* (2013.01); *G01N 30/72* (2013.01); *G01N 2021/7786* (2013.01); *G01N 2030/025* (2013.01); *G01N 2030/027* (2013.01)

(58) Field of Classification Search
CPC ... G01N 21/77; G01N 21/783; G01N 33/0013
USPC .............................. 422/86, 91; 436/135–136
See application file for complete search history.

(56) References Cited

U.S. PATENT DOCUMENTS

| | | | | | |
|---|---|---|---|---|---|
| 2,849,291 | A | * | 8/1958 | Allison | ................ G01N 21/783 436/135 |
| 2,862,963 | A | * | 12/1958 | Fuchs | ..................... C07C 63/26 562/480 |
| 2,877,219 | A | * | 3/1959 | Ito | .......................... C09B 29/06 534/860 |
| 3,303,341 | A | * | 2/1967 | Fram | ....................... H01J 29/10 430/5 |
| 3,406,063 | A | * | 10/1968 | Matkan | ................ G03G 5/0514 430/69 |

(Continued)

FOREIGN PATENT DOCUMENTS

| CN | 1275075 A | 11/2000 |
|---|---|---|
| CN | 1412553 A | 4/2003 |

(Continued)

OTHER PUBLICATIONS

Silva, M. A. R et al, Journal of Physical Chemistry A 2002, 106, 8820-8826.*

(Continued)

*Primary Examiner* — Arlen Soderquist

(57) ABSTRACT

An OH radical detection probe (102) includes an aromatic carboxylic acid, a polar aprotic organic solvent, and a polar protic organic solvent.

7 Claims, 11 Drawing Sheets

(56) References Cited

U.S. PATENT DOCUMENTS

| | | | | |
|---|---|---|---|---|
| 3,632,760 A * | 1/1972 | Shen | C07C 229/38 | 514/166 |
| 3,646,200 A * | 2/1972 | Shen | C07C 317/00 | 514/159 |
| 3,652,665 A * | 3/1972 | Shen | C07C 317/00 | 562/474 |
| 4,164,585 A * | 8/1979 | Sawyer | C07D 307/62 | 514/474 |
| 4,172,960 A * | 10/1979 | Baldwin | C07C 37/055 | 568/650 |
| 4,459,225 A * | 7/1984 | Teetz | C07K 14/702 | 530/330 |
| 4,765,961 A * | 8/1988 | Schiff | G01N 21/766 | 422/52 |
| 4,912,051 A * | 3/1990 | Zaromb | G01N 1/2205 | 422/52 |
| 5,047,540 A * | 9/1991 | Kamata | C07C 391/00 | 546/172 |
| 5,049,681 A * | 9/1991 | Sato | C07F 7/1804 | 549/206 |
| 5,218,000 A * | 6/1993 | Usherwood | A61P 25/18 | 514/617 |
| 5,328,851 A * | 7/1994 | Zaromb | G01N 1/2205 | 261/104 |
| 6,033,459 A * | 3/2000 | Hase | G01N 30/06 | 95/82 |
| 6,093,831 A * | 7/2000 | Rapoport | C07D 263/44 | 548/227 |
| 6,465,420 B1 | 10/2002 | Perring et al. | | |
| 6,545,049 B1 * | 4/2003 | Canan-Koch | A61P 17/00 | 514/569 |
| 8,809,064 B2 | 8/2014 | Miller | | |
| 2001/0042843 A1 * | 11/2001 | Cox | G01N 33/0039 | 250/504 R |
| 2002/0016460 A1 * | 2/2002 | Snow | C07D 471/04 | 544/238 |
| 2002/0120165 A1 * | 8/2002 | Zaworotko | C07F 1/08 | 560/76 |
| 2003/0096730 A1 | 5/2003 | Perring et al. | | |
| 2003/0199565 A1 * | 10/2003 | Kalindjian | C07D 417/04 | 514/381 |
| 2004/0175837 A1 * | 9/2004 | Bonne | G01N 21/05 | 436/164 |
| 2004/0214340 A1 | 10/2004 | Kajii | | |
| 2004/0241868 A1 * | 12/2004 | Cox | G01N 33/0039 | 436/116 |
| 2007/0254869 A1 * | 11/2007 | Cao | C07D 223/32 | 514/217 |
| 2008/0015199 A1 * | 1/2008 | Clark | C07D 401/14 | 514/252.05 |
| 2008/0132477 A1 * | 6/2008 | Betschart | A61P 43/00 | 514/183 |
| 2008/0194668 A1 * | 8/2008 | Marsilje | A61P 37/06 | 514/415 |
| 2008/0306064 A1 * | 12/2008 | Brown | A61P 25/00 | 514/234.5 |
| 2009/0029903 A1 * | 1/2009 | Swinnen | C07C 63/66 | 514/1.1 |
| 2009/0076275 A1 * | 3/2009 | Bolin | C07D 413/14 | 546/119 |
| 2009/0082365 A1 * | 3/2009 | Bhalay | A61P 1/18 | 514/255.05 |
| 2009/0163471 A1 * | 6/2009 | Rice | A61P 1/16 | 514/210.21 |
| 2009/0221587 A1 * | 9/2009 | Jeanguenat | A01N 43/60 | 514/243 |
| 2009/0275583 A1 * | 11/2009 | Yager | C07J 63/008 | 514/237.8 |
| 2010/0179153 A1 * | 7/2010 | Mattes | A61P 5/24 | 514/248 |
| 2010/0324043 A1 * | 12/2010 | Claffey | A61P 9/00 | 514/235.2 |
| 2011/0039853 A1 * | 2/2011 | Ebdrup | C07D 295/088 | 514/239.2 |
| 2012/0085235 A1 * | 4/2012 | De Weireld | B01J 20/226 | 95/136 |
| 2012/0231549 A1 | 9/2012 | Miller | | |
| 2012/0329168 A1 * | 12/2012 | Lin | G01N 21/783 | 436/144 |
| 2014/0190436 A1 | 7/2014 | Inubushi et al. | | |
| 2014/0200361 A1 * | 7/2014 | Lee | C07C 63/333 | 556/42 |
| 2015/0111914 A1 * | 4/2015 | Bell | A61P 29/00 | 514/278 |
| 2015/0353382 A1 | 12/2015 | Toshiba | | |
| 2016/0159815 A1 * | 6/2016 | Deninno | C07D 403/06 | 514/259.3 |
| 2017/0122954 A1 | 5/2017 | Lebedeva et al. | | |
| 2017/0348682 A1 * | 12/2017 | Katz | B01D 53/54 | |
| 2021/0164909 A1 * | 6/2021 | Kurata | G01N 21/783 | |

FOREIGN PATENT DOCUMENTS

| | | |
|---|---|---|
| CN | 101042371 A | 9/2007 |
| CN | 101241076 A | 8/2008 |
| CN | 101482545 A | 7/2009 |
| CN | 103149188 A | 6/2013 |
| CN | 103630510 A | 3/2014 |
| CN | 103748064 A | 4/2014 |
| CN | 103969238 A | 8/2014 |
| EP | 2 746 248 A1 | 6/2014 |
| EP | 2 941 955 A1 | 11/2015 |
| JP | 2003-075347 A | 3/2003 |
| JP | 2012-098114 A | 5/2012 |
| JP | 2014-130105 A | 7/2014 |
| JP | 2014-166969 A | 9/2014 |
| JP | 5703283 B2 | 4/2015 |
| JP | 5740138 B2 | 6/2015 |
| JP | 2016-171792 A | 9/2016 |
| JP | 2016-185083 A | 10/2016 |
| SU | 387952 * | 10/1973 |
| WO | 2013/024761 A1 | 2/2013 |
| WO | 2014/103440 A1 | 7/2014 |
| WO | 2014/104350 A1 | 7/2014 |

OTHER PUBLICATIONS

Pezo, D. et al, Analytical and Bioanalytical Chemmistry 2006, 385, 1241-1246.*

Katz, M. J. et al, Chemmical Communications 2013, 49, 9449-9451.*

Dimitrie, J. M. et al, RSC Advances 2014, 4, 32228-32236.*

Setsukinai, K. et al, Journal of Biological Chemistry 2003, 278, 3170-3175.*

Freinbichler, W. et al, Journal of Neurochemistry 2008, 105, 738-749.*

Fisher, S. C. et al, Geochemical Transactions 2012, 13, paper 3, 18 pages.*

Li, X., Food Chemistry 2013, 141, 2083-2088.*

Li, S. et al, IEEE Transactions on Dielectrics and Electrical Insulation 2015, 22, 1856-1865.*

Son, Y. et al, International Journal of Environmental Research and Public Health 2015, 12, 13678-13695.*

Badmus, K. Analytical and Bioanalytical Chemistry Research 2016, 3, 139-147.*

Arlos, M. J. et al, Journal of Environmental Chemical Engineering 2017, 5, 4497-4504 with 11 pages of supplemenrtary Information.*

European Patent Office, "Extended European Search Report," issued in European Patent Application No. 18 757 228.4, which is a counterpart to U.S. Appl. No. 16/545,342, dated Nov. 13, 2020, 8 pages.

Seiji Kanazawa et al., "Observation of OH radicals produced by pulsed discharges on the surface of a liquid," Plasma Sources Science and Technology, vol. 20, No. 3, pp. 1-8 (2011), IOP Publishing Ltd.

Nobuaki Shimizu et al., "Sonocatalytic facilitation of hydroxyl radical generation in the presence of TiO2," Ultrasonics Sonochemistry, vol. 15, pp. 988-994 (2008), Elsevier B.V.

(56) References Cited

OTHER PUBLICATIONS

China National Intellectual Property Administration, "First Office Action," issued in Chinese Patent Application No. 201880011497.3, which is a Chinese counterpart of U.S. Appl. No. 16/545,342, dated Apr. 28, 2021, 8 pages.

Takanori Iijima et al., "OH Radical Generator for Waste Water Treatment Containing Recalcitrant Organic Matter," Toshiba Review, vol. 61, No. 8, pp. 40-43 (2006).

V. Nahuel Montesinos et al., "Detection and quantification of reactive oxygen species (ROS) in indoor air," Talanta, vol. 138, pp. 20-27 (2015), Elsevier B.V.

International Search Report, received for PCT Patent Application No. PCT/JP2018/004931, dated May 1, 2018, 6 pages (3 pages of English translation of International Search Report, and 3 pages of original International Search Report).

* cited by examiner

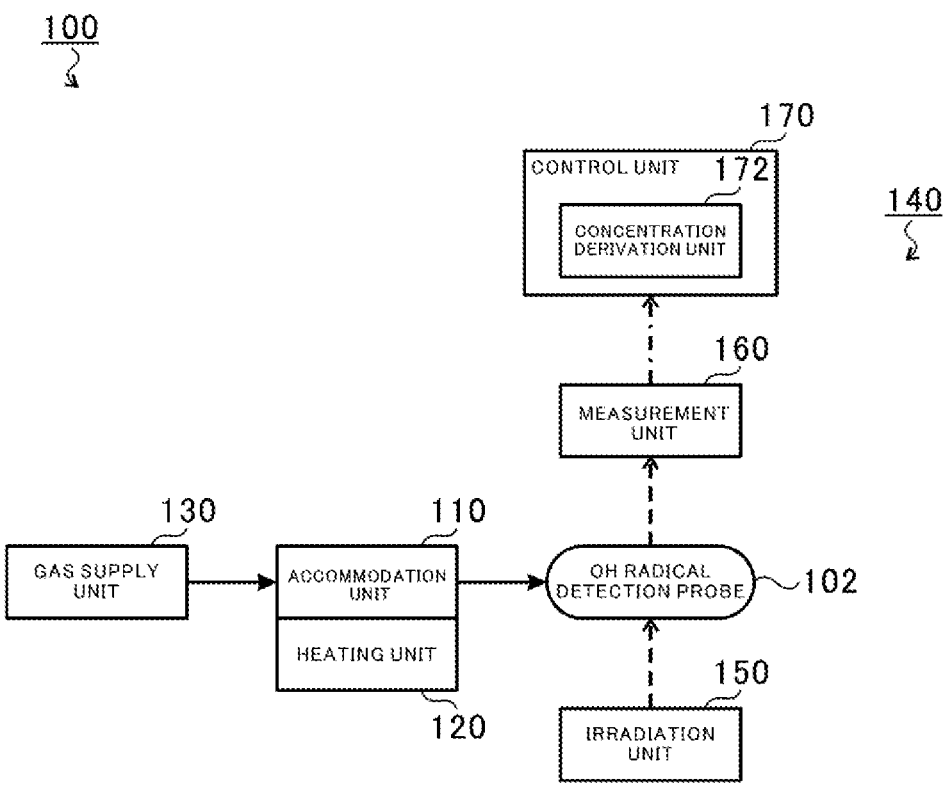

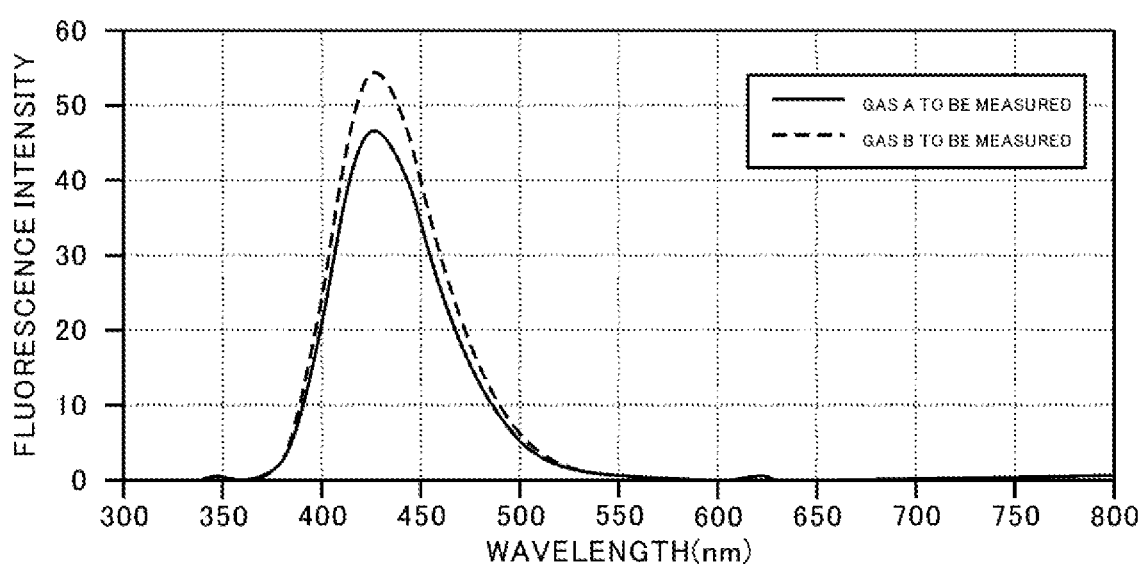

OH RADICAL MEASUREMENT DEVICE AND METHOD USING AN OH RADICAL DETECTION PROBE

The present disclosure relates to an OH radical detection probe, an OH radical measurement device, and an OH radical measurement method. This application is a continuation application of International Application No. PCT/JP2018/004931, filed on Feb. 13, 2018, which claims priority from Japanese Patent Application No. 2017-032024, filed on Feb. 23, 2017, the contents of which are incorporated herein by reference in their entirety.

TECHNICAL FIELD

Background Art

As a technology for measuring an OH radical in water, a technology involving deriving a concentration of an OH radical by measuring a concentration of hydroxyterephthalic acid has hitherto been developed (for example, Patent Literature 1). The technology of Patent Literature 1 involves generating an OH radical by discharging an electric current in an aqueous solution containing terephthalic acid and measuring a concentration of hydroxyterephthalic acid generated by a reaction between the generated OH radical and terephthalic acid.

CITATION LIST

Patent Literature

Patent Literature 1: Japanese Patent No. 5740138 B2

SUMMARY

Technical Problem

As described in Patent Literature 1, a technology for detecting an OH radical in a liquid phase has hitherto been developed. However, a probe technology for detecting an OH radical in a gas phase has not been developed.

In view of the above-mentioned problem, an object of the present disclosure is to provide an OH radical detection probe, an OH radical measurement device, and an OH radical measurement method, which are capable of detecting an OH radical in a gas phase.

Solution to Problem

In order to solve the above-mentioned problem, according to one embodiment of the present disclosure, there is provided an OH radical detection probe, including: an aromatic carboxylic acid; a polar aprotic organic solvent; and a polar protic organic solvent.

In addition, a content of the polar protic organic solvent may be lower than a content of the polar aprotic organic solvent.

In addition, the aromatic carboxylic acid may include one or a plurality of compounds selected from the group consisting of terephthalic acid, salicylic acid, 4-hydroxybenzoic acid, and phenylalanine.

In addition, the polar aprotic organic solvent may include N,N-dimethylformamide, and the polar protic organic solvent play include methanol.

In order to solve the above-mentioned problem, according to one embodiment of the present disclosure, there is provided an OH radical measurement device, including: an accommodation unit configured to accommodate an OH radical detection probe including an aromatic carboxylic acid, a polar aprotic organic solvent, and a polar protic organic solvent; a gas supply unit configured to supply a gas to be measured into the accommodation unit; and a concentration conversion unit configured to convert a concentration of an OH radical in the gas to be measured based on a concentration of a reaction product of the aromatic carboxylic acid and the OH radical in the OH radical detection probe after being brought into contact with the gas to be measured.

In addition, the concentration conversion unit may include: an irradiation unit configured to irradiate the OH radical detection probe after being brought into contact with the gas to be measured with UV light; a measurement unit configured to measure an intensity of fluorescence generated from the OH radical detection probe; and a concentration derivation unit configured to derive a concentration of the OH radical in the gas to be measured based on the intensity of the fluorescence measured by the measurement unit.

In addition, the concentration conversion unit may include any one or any two or more of a gas chromatograph, a liquid chromatograph, a mass spectrometer, a gas chromatograph-mass spectrometer, a liquid chromatograph-mass spectrometer, and an infrared spectrometer.

In addition, the OH radical measurement device may further include a heating unit configured to heat the gas to be measured in the accommodation unit.

In order to solve the above-mentioned problem, according to one embodiment of the present disclosure, there is provided an OH radical measurement method, including measuring an OH radical in a gas phase through use of an OH radical detection probe including an aromatic carboxylic acid, a polar aprotic organic solvent, and a polar protic organic solvent.

In addition, the OH radical measurement method may include the steps of: bringing the OH radical detection probe into contact with a gas to be measured; and converting a concentration of an OH radical in the gas to be measured based on a concentration of a reaction product of the aromatic carboxylic acid and the OH radical in the OH radical detection probe after being brought into contact with the gas to be measured.

Effects of Disclosure

The OH radical in the gas phase can be detected.

BRIEF DESCRIPTION OF DRAWINGS

FIG. 1 is a view for illustrating an OH radical measurement device.

FIG. 2 is a view for illustrating a specific configuration of an accommodation unit, a heating unit, and a gas supply unit.

FIG. 5 is a graph for showing fluorescence spectra of Example 2.

DESCRIPTION OF EMBODIMENTS

Figure 3:
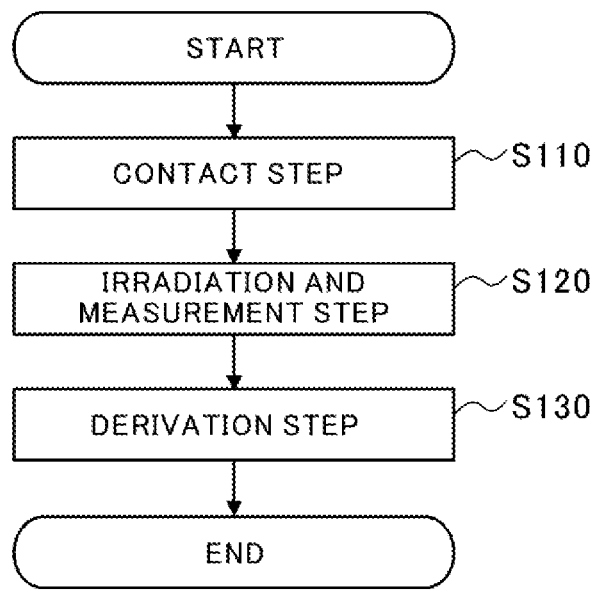
FIG. 3 is a flowchart for illustrating a flow of processing of an OH radical measurement method.

Now, with reference to the attached drawings, an embodiment of the present disclosure is described in detail. The dimensions, materials, and other specific numerical values represented in the embodiment are merely examples used for facilitating the understanding of the disclosure, and do not limit the present disclosure unless otherwise noted. Elements having substantially the same functions and configurations herein and in the drawings are denoted by the same reference symbols to omit redundant description thereof. Further, illustration of elements with no direct relationship to the present disclosure is omitted.

[OH Radical Detection Probe]

An OH radical detection probe according to this embodiment includes an aromatic carboxylic acid, a polar aprotic organic solvent, and a polar protic organic solvent. When the OH radical detection probe includes the polar protic organic solvent, the aromatic carboxylic acid, and an OH radical can be caused to react with each other, and thus the OH radical can be detected.

In addition, a related-art OH radical detection probe configured to measure an OH radical in a liquid phase is an aqueous solution that uses water as a solvent for dissolving terephthalic acid. Therefore, when an attempt is made to measure an OH radical in a gas phase, in particular, water vapor (or in a humidified gas phase having a high humidity) with the related-art OH radical detection probe, an OH radical generated from an OH radical precursor dissolved in the aqueous solution and terephthalic acid preferentially react with each other. Thus, the related-art OH radical detection probe has a problem in that the OH radical in the gas phase cannot be selectively detected.

In contrast, the OH radical detection probe according to this embodiment uses a non-aqueous solvent containing the polar aprotic organic solvent as a main solvent, and hence an OH radical precursor is not dissolved in a liquid phase. Thus, the OH radical detection probe according to this embodiment can prevent the situation in which the OH radical generated from the OH radical precursor dissolved in the liquid phase and the aromatic carboxylic acid react with each other, unlike an aqueous solvent (aqueous solution).

In addition, when the OH radical and the aromatic carboxylic acid react with each other, a proton ($H^+$) is generated. Therefore, when only the polar aprotic organic solvent is used as an organic solvent for dissolving the aromatic carboxylic acid, the proton is not accepted, and the reaction between the OH radical and the aromatic carboxylic acid does not proceed.

In view of the foregoing, the OH radical detection probe according to this embodiment includes the polar protic organic solvent as a sub-solvent, and hence the proton generated by the reaction can be accepted. With this, the reaction between the OH radical and the aromatic carboxylic acid can proceed to generate hydroxyterephthalic acid (hereinafter referred to as "HTA"), with the result that an OH radical in a gas phase can be detected. In particular, the OH radical detection probe according to this embodiment can detect an OH radical in water vapor or in a humidified gas phase having a high humidity. In this case, the "gas phase" has a concept encompassing a gas containing a liquid (for example, liquid water) as well as a phase in which only a gas is present. The gas containing a liquid is a gas containing a mist, a gas including a liquid layer (for example, a gas including portions in which water molecules are formed into a plurality of layers), or a gas in which a liquid is dispersed (aerosol).

The content of the aromatic carboxylic acid in the solvent (polar aprotic organic solvent and polar protic organic solvent) in the OH radical detection probe is, for example, about 2 mmol/L (2 mM=2 mol/m$^3$). In addition, it is preferred that the content of the polar protic organic solvent in the OH radical detection probe be lower than the content of the polar aprotic organic solvent (for example, the content of the polar protic organic solvent be from about 10% to about 50% of the content of the polar aprotic organic solvent). With this, the amount of moisture in the gas phase dissolved in the polar protic organic solvent can be reduced.

In addition, the aromatic carboxylic acid forming the OH radical detection probe according to this embodiment is one or a plurality of compounds selected from the group consisting of phthalic acid (o-phthalic acid, m-phthalic acid, and p-phthalic acid (terephthalic acid)), derivatives of phthalic acid (for example, dimethyl terephthalate), benzoic acid, derivatives of benzoic acid (for example, hydroxybenzoic acid (2-hydroxybenzoic acid (salicylic acid), 3-hydroxybenzoic acid, and 4-hydroxybenzoic acid)), and a compound in which a carboxyl group is bonded to a benzene ring through a substituent. The aromatic carboxylic acid is preferably one or a plurality of compounds selected from the group consisting of terephthalic acid, salicylic acid, 4-hydroxybenzoic acid, and phenylalanine.

In addition, the polar aprotic organic solvent forming the OH radical detection probe according to this embodiment is, for example, one or a plurality of compounds selected from the group consisting of N,N-dimethylformamide (DMF), tetrahydrofuran (THF), acetone, acetonitrile, dimethyl sulfoxide (DMSO), dioxane, chloroform, ethylene dichloride, and methylene chloride.

In addition, the polar protic organic solvent forming the OH radical detection probe according to this embodiment is one or a plurality of compounds selected from the group consisting of methanol, ethanol, 1-propanol, 2-propanol (isopropanol), acetic acid, ethyl acetate, formic acid, 1-butanol, isobutyl alcohol, ethylene glycol, and methanediol.

[Production Method for OH Radical Detection Probe]

Subsequently, a production method for an OH radical detection probe is described. First, an aromatic carboxylic acid is dissolved in a polar aprotic organic solvent. Then, a polar protic organic solvent is mixed with the polar aprotic organic solvent solution of the aromatic carboxylic acid. With this, the aromatic carboxylic acid can be dispersed in the solvent.

[OH Radical Measurement Device 100]

FIG. 1 is a view for illustrating an OH radical measurement device 100. In FIG. 1, a flow of a gas or a liquid is represented by the solid line arrow, a flow of light is represented by the broken line arrow, and a flow of a signal is represented by the dashed-dotted line arrow.

As illustrated in FIG. 1, the OH radical measurement device 100 includes an accommodation unit 110, a heating unit 120, a gas supply unit 130, and a concentration conversion unit 140.

The accommodation unit 110 is configured to accommodate an OH radical detection probe 102 (liquid) described above. The heating unit 120 is configured to heat a gas to be measured and the OH radical detection probe 102 in the accommodation unit 110 to a predetermined temperature when the humidity in a gas phase is high. The gas supply unit 130 is configured to supply the gas to be measured into the accommodation unit 110.

FIG. 2 is a view for illustrating a specific configuration of the accommodation unit 110, the heating unit 120, and the gas supply unit 130. In FIG. 2, a flow of the gas to be measured is represented by the solid line arrow, and a flow of the gas after contact is represented by the broken line arrow. As illustrated in FIG. 2, the accommodation unit 110 is a sealed container. The OH radical detection probe 102 is accommodated in an inner space 110a of the accommodation unit 110.

The heating unit 120 is configured to heat the gas to be measured and the OH radical detection probe 102 in the accommodation unit 110 when the gas to be measured has a high humidity. The heating unit 120 is formed of, for example, a heater surrounding the accommodation unit 110. With the configuration including the heating unit 120, when the gas to be measured has a high humidity, the situation in which moisture is condensed to generate liquid water can be prevented in the accommodation unit 110.

The gas supply unit 130 includes an inner pipe 132, an outer pipe 134, and an exhaust pipe 136. The inner pipe 132 is a pipe having one end 132a connected to a gas supply source (not shown) and another end 132b arranged in the inner space 110a of the accommodation unit 110. The outer pipe 134 is a pipe surrounding part of the inner pipe 132, and having one end 134a arranged in the inner space 110a of the accommodation unit 110 and another end 134b connected to the exhaust pipe 136. The other end 132b of the inner pipe 132 is positioned vertically below (on an OH radical detection probe 102 side of) the one end 134a of the outer pipe 134.

Thus, the gas to be measured, which has been supplied by the gas supply unit 130, reaches the inner space 110a of the accommodation unit 110 from the other end 132b of the inner pipe 132. Then, the gas to be measured flows into the outer pipe 134 from the one end 134a of the outer pipe 134 after being brought into contact with the OH radical detection probe 102 in the inner space 110a. The gas to be measured, which has flowed into the outer pipe 134, is discharged to the outside through the exhaust pipe 136.

Returning to FIG. 1, the concentration conversion unit 140 is configured to convert the concentration of an OH radical in the gas to be measured based on the concentration of a reaction product (HTA) of the aromatic carboxylic acid (terephthalic acid) and the OH radical in the OH radical detection probe 102 after being brought into contact with the gas to be measured. In this embodiment, the concentration conversion unit 140 includes an irradiation unit 150, a measurement unit 160, and a control unit 170.

The irradiation unit 150 is configured to irradiate the OH radical detection probe 102 taken out of the accommodation unit 110 with UV light (for example, UV light having a wavelength of 310 nm). The measurement unit 160 is configured to measure the intensity of fluorescence (for example, fluorescence having a wavelength of 425 nm indicating hydroxyterephthalic acid (HTA)) generated from the OH radical detection probe 102 through the irradiation with UV light by the irradiation unit 150.

The control unit 170 is formed of a semiconductor integrated circuit including a central processing unit (CPU). The control unit 170 is configured to read a program, a parameter, and the like for operating the CPU itself from a ROM and manage and control the entire OH radical measurement device 100 in cooperation with a RAM and other electronic circuits serving as a work area. In this embodiment, the control unit 170 functions as a concentration derivation unit 172.

The concentration derivation unit 172 is configured to derive the concentration of the OH radical in the gas to be measured based on the intensity of the fluorescence measured by the measurement unit 160.

For example, in the case where terephthalic acid is adopted as the aromatic carboxylic acid forming the OH radical detection probe 102, when the OH radical is brought into contact with the OH radical detection probe 102, a reaction represented by the following reaction formula (1) proceeds.

Reaction formula (1)

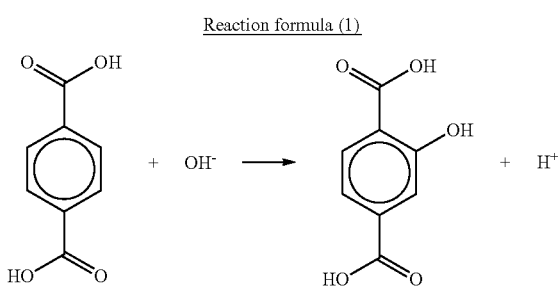

The reaction formula (1) may also be expressed as terephthalic acid+OH radical-2-hydroxyterephthalic acid (HTA)+proton.

Thus, in this case, terephthalic acid reacts with the OH radical to generate 2-hydroxyterephthalic acid (HTA) and a proton. Therefore, when the OH radical detection probe 102 is irradiated with UV light by the irradiation unit 150, fluorescence is generated from HTA. Then, the measurement unit 160 measures the intensity of fluorescence generated from HTA (fluorescence intensity), with the result that the concentration of HTA, that is, the concentration of the OH radical in the gas phase (in the gas to be measured) can be calculated based on the fluorescence intensity.

Thus, a calibration curve of the fluorescence intensity of HTA can be created by preparing a plurality of reference solutions having different HTA concentrations, and irradiating each of the solutions with UV light to measure a fluorescence intensity. Therefore, the concentration derivation unit 172 can derive the concentration of the OH radical based on the intensity of the fluorescence measured by the measurement unit 160 and the calibration curve.

[OH Radical Measurement Method]

Subsequently, an OH radical measurement method using the OH radical measurement device 100 is described. FIG. 3 is a flowchart for illustrating a flow of processing of the OH radical measurement method. The OH radical measurement method includes a contact step S110, an irradiation and measurement step S120, and a derivation step S130.

[Contact Step S110]

The contact step S110 is a step of bringing the OH radical detection probe 102 and the gas to be measured into contact with each other under a predetermined temperature. Specifically, first, the OH radical detection probe 102 is accommodated in the accommodation unit 110. Then, when the gas to be measured is supplied to the inner space 110a of the accommodation unit 110 by the gas supply unit 130, the OH radical detection probe 102 and the gas to be measured are brought into contact with each other. When the gas to be measured has a high humidity, the gas to be measured and the OH radical detection probe 102 in the accommodation unit 110 are heated to a predetermined temperature by driving the heating unit 120.

[Irradiation and Measurement Step S120]

In the irradiation and measurement step S120, first, the OH radical detection probe 102 after being brought into contact with the gas to be measured in the contact step S110 is taken out. Then, the irradiation unit 150 irradiates the OH radical detection probe 102 thus taken out with UV light, and the measurement unit 160 measures the intensity of fluorescence generated from the OH radical detection probe 102.

[Derivation Step S130]

The derivation step S130 is a step in which the concentration derivation unit 172 derives the concentration of the OH radical in the gas to be measured based on the intensity of the fluorescence measured in the irradiation and measurement step S120.

As described above, according to the OH radical measurement device 100 of this embodiment and the OH radical measurement method using the OH radical measurement device 100, through use of an organic solvent other than water as a solvent of the OH radical detection probe 102, an OH radical in a gas phase can be measured.

EXAMPLES

Example 1

Calibration curves for a chemical probe of Comparative Example 1 (related-art example) and an OH radical detection probe of Example 1 were created, and comparison in measurement sensitivity was made.

First, a reference solution group (Comparative Example 1) in which HTA was dissolved in water at a predetermined concentration was prepared. Then, a reference solution group (Example 1) in which HTA was dissolved in DMF and methanol (volume ratio of 4:1) at a predetermined concentration was prepared. Calibration curves of the fluorescence intensity of HTA of Comparative Example 1 and Example 1 were created. Both in Comparative Example 1 and Example 1, reference solutions having the above-mentioned predetermined concentration (concentration of HTA) of 0.002 µM, 0.2 µM, and 20 µM were used.

Figure 4A:
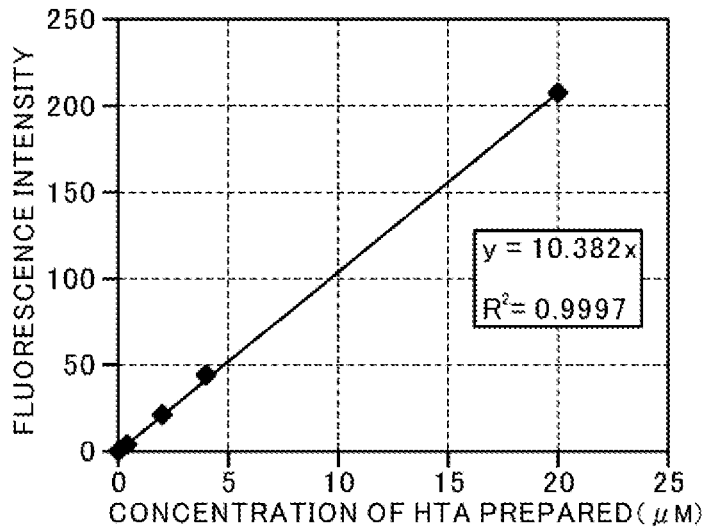
FIG. 4A is a graph for showing a calibration curve of Comparative Example 1.
Figure 4B:
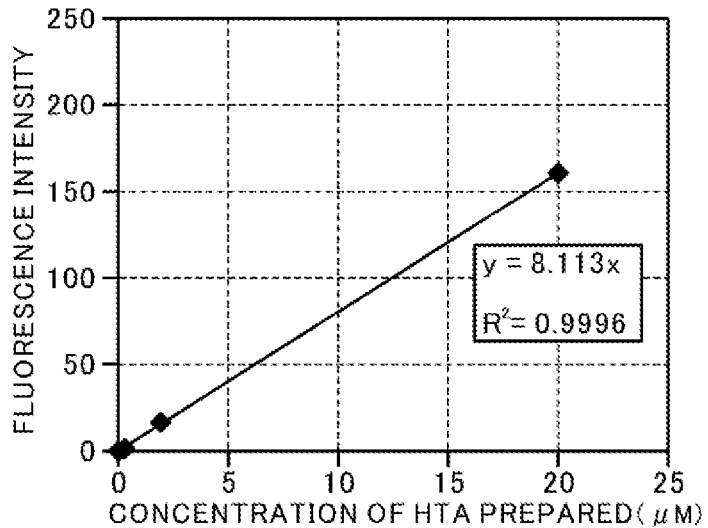
FIG. 4B is a graph for showing a calibration curve of Example 1.

FIG. 4A and FIG. 4B are graphs for showing the calibration curves of Comparative Example 1 and Example 1. FIG. 4A is a graph for showing the calibration curve of Comparative Example 1. FIG. 4B is a graph for showing the calibration curve of Example 1. As shown in FIG. 4A, in Comparative Example 1, the calibration curve satisfying $y=10.382x$ ($R^2=0.9997$) was obtained. In addition, as shown in FIG. 4B, in Example 1, the calibration curve satisfying $y=8.113x$ ($R^2=0.9996$) was obtained.

With this, it was confirmed that the calibration curve having the same slope and the same correlation coefficient as those in Comparative Example 1 as related art was able to be created also in Example 1. As a result, it was verified that the OH radical detection probe of Example 1 using an organic solvent also exhibited the performance equivalent to that of the related-art chemical probe of Comparative Example 1 using an aqueous solution.

Example 2

A gas A to be measured and a gas B to be measured were measured through use of a chemical probe of Comparative Example 2 (related-art example). As the chemical probe of Comparative Example 2, a 2 mM sodium terephthalate aqueous solution was prepared. In addition, as the gas A to be measured, a mixed gas of ozone and water vapor was used. As the gas B to be measured, dried ozone was used.

Moreover, the chemical probe of Comparative Example 2 after being brought into contact with the gas A to be measured for 5 minutes was irradiated with UV light, and the intensity of fluorescence generated from the chemical probe of Comparative Example 2 was measured. In addition, the chemical probe of Comparative Example 2 after being brought into contact with the gas B to be measured for 5 minutes was irradiated with UV light, and the intensity of fluorescence generated from the chemical probe of Comparative Example 2 was measured.

FIG. 5 is a graph for showing fluorescence spectra of Example 2. In FIG. 5, the result obtained by bringing the gas A to be measured into contact with the chemical probe of Comparative Example 2 is represented by the solid line, and the result obtained by bringing the gas B to be measured into contact with the chemical probe of Comparative Example 2 is represented by the broken line.

As shown in FIG. 5, when the gas A to be measured was brought into contact with the chemical probe of Comparative Example 2, the intensity of fluorescence having a wavelength of 425 nm indicating HTA that was a reaction product with an OH radical was about 47. In addition, when the gas B to be measured was brought into contact with the chemical probe of Comparative Example 2, the intensity of fluorescence having a wavelength of 425 nm indicating HTA was about 54. That is, no significant difference was recognized in fluorescence intensity between the case in which the gas A to be measured was brought into contact with the chemical probe of Comparative Example 2 and the case in which the gas B to be measured was brought into contact with the chemical probe of Comparative Example 2. In other words, it was confirmed that the chemical probe of Comparative Example 2 detected an OH radical irrespective of whether or not the gas to be measured contained water vapor.

It has hitherto been known that a microbicidal effect was not recognized only with ozone (dried ozone), though ozone exhibited a microbicidal effect in the presence of water (for example, New Ozone Technology and Biotechnology, Senichi Masuda, J.IEE Japan, Vol. 108, No. 12, 1988 p. 1173-1176, and Technology of Ozone Application to Microorganism Control in Food Factory, Shigezo Naito, http://www.mac.or.jp/mail/120102/04.shtml). It has been known that an OH radical contributes to a microbicidal effect, and hence it is assumed that an OH radical is not generated only with ozone. That is, ozone does not generate an OH radical without coexisting with water, and a generated OH radical exhibits a microbicidal effect.

However, as shown in FIG. 5, according to the results of Example 2, even when the gas A to be measured containing water vapor was brought into contact with the chemical probe of Comparative Example 2, and even when the gas B to be measured containing no water vapor was brought into contact with the chemical probe of Comparative Example 2, OH radicals were detected. That is, it was found that the chemical probe of Comparative Example 2 merely detected an OH radical generated by a reaction between water and ozone in the chemical probe. In other words, it was confirmed that the chemical probe of Comparative Example 2 (related-art chemical probe) was not able to selectively detect an OH radical in the gas to be measured.

Example 3: Measurement of Only Ozone as Gas to be Measured

As an OH radical detection probe, a solution in which 2 mmol/L of terephthalic acid was dissolved in DMF and methanol (volume ratio of 4:1) was used. In addition, ozone was used as a gas to be measured. In Example 3, heating by the heating unit 120 was not performed. Moreover, the OH radical detection probe after being brought into contact with ozone was irradiated with UV light, and the intensity of fluorescence generated from the OH radical detection probe was measured.

Figure 6A:
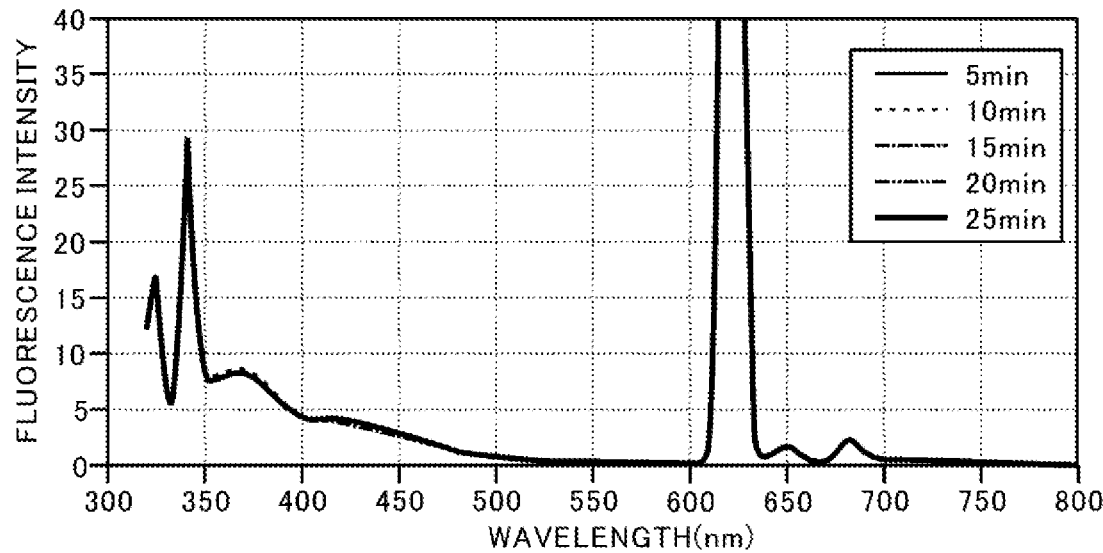
FIG. 6A is a graph for showing fluorescence spectra of Example 3.
Figure 6B:
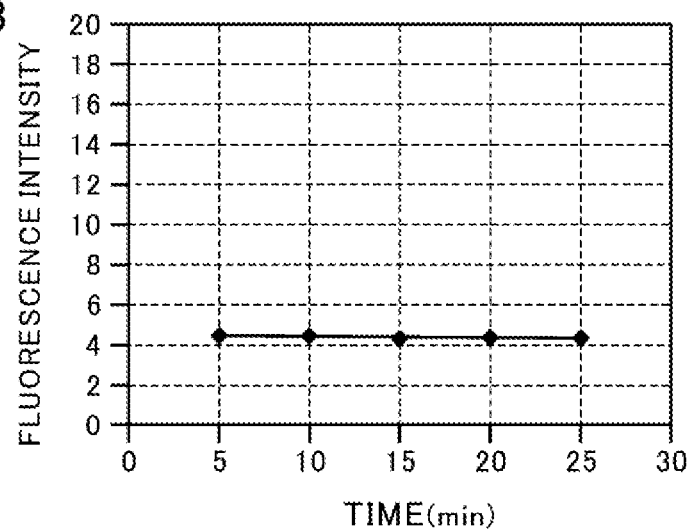
FIG. 6B is a graph for showing a relationship between: a contact time (min) of a gas to be measured and an OH radical detection probe; and a fluorescence intensity in Example 3.
Figure 6C:
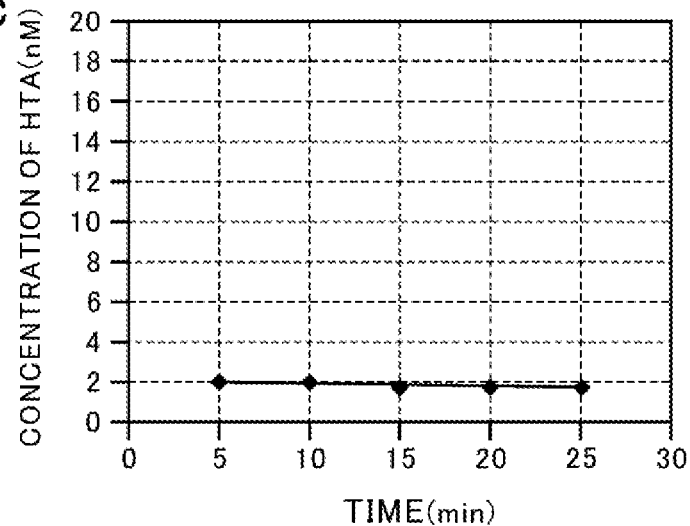
FIG. 6C is a graph for showing a relationship between: the contact time (min) of the gas to be measured and the OH radical detection probe; and a concentration (nM) of HTA in the OH radical detection probe in Example 3.

FIG. 6A to FIG. 6C are graphs for showing the results of Example 3. FIG. 6A is a graph for showing fluorescence spectra of Example 3. FIG. 6B is a graph for showing a relationship between: a contact time (min) of the gas to be measured and the OH radical detection probe; and the fluorescence intensity in Example 3. FIG. 6C is a graph for showing a relationship between: the contact time (min) of the gas to be measured and the OH radical detection probe; and the concentration (nM) of HTA in the OH radical detection probe in Example 3.

As shown in FIG. 6A to FIG. 6C, in any of the cases of a contact time of 5 minutes, 10 minutes, 15 minutes, 20 minutes, and 25 minutes, fluorescence having a wavelength of 425 nm indicating HTA that was a reaction product with an OH radical was not detected only with dried ozone.

Example 4: Measurement of Mixed Gas of Ozone and Water Vapor as Gas to be Measured As an OH radical detection probe, a solution in which 2 mmol/L of terephthalic acid was dissolved in DMF and methanol (volume ratio of 4:1) was used. In addition, a mixed gas of ozone and water vapor was used as a gas to be measured. In Example 4, heating was performed at 60° C. by the heating unit 120. Moreover, the OH radical detection probe after being brought into contact with the mixed gas of ozone and water vapor was irradiated with UV light, and the intensity of fluorescence generated from the OH radical detection probe was measured.

Figure 7A:
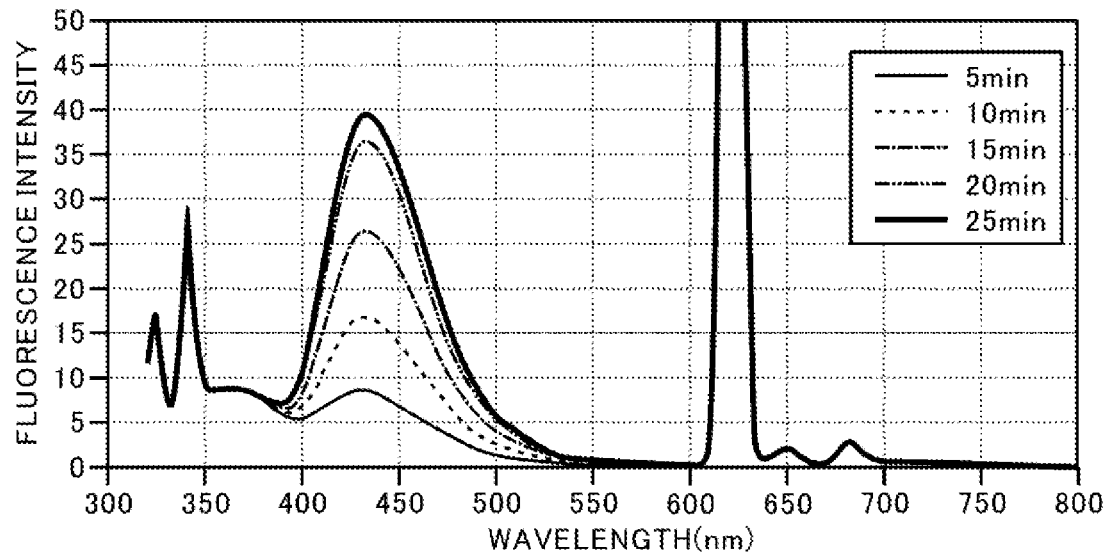
FIG. 7A is a graph for showing fluorescence spectra of Example 4.
Figure 7B:
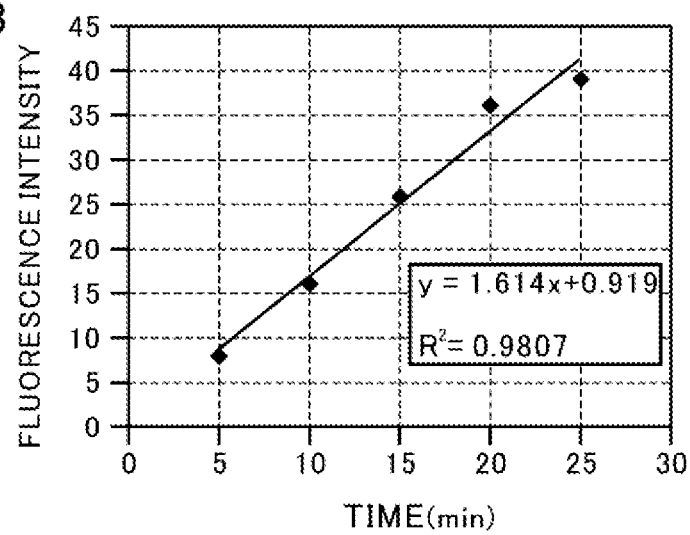
FIG. 7B is a graph for showing a relationship between: a contact time (min) of a gas to be measured and an OH radical detection probe; and a fluorescence intensity in Example 4.
Figure 7C:
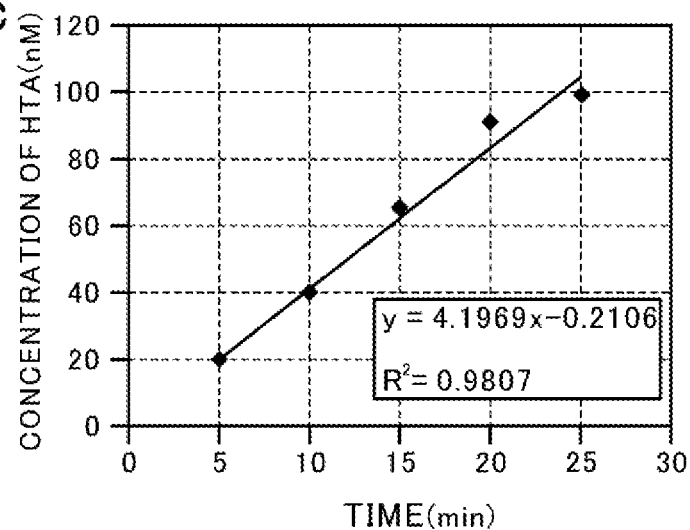
FIG. 7C is a graph for showing a relationship between: the contact time (min) of the gas to be measured and the OH radical detection probe; and a concentration (nM) of ETA in the OH radical detection probe in Example 4.

FIG. 7A to FIG. 7C are graphs for showing the results of Example 4. FIG. 7A is a graph for showing fluorescence spectra of Example 4. FIG. 7B is a graph for showing a relationship between: a contact time (min) of the gas to be measured and the OH radical detection probe; and the fluorescence intensity in Example 4. FIG. 7C is a graph for showing a relationship between: the contact time (min) of the gas to be measured and the OH radical detection probe; and the concentration (nM) of HTA in the OH radical detection probe in Example 4.

As shown in FIG. 7A and FIG. 7B, it was found that, as the contact time increased to 5 minutes, 10 minutes, 15 minutes, 20 minutes, and 25 minutes, the intensity of fluorescence having a wavelength of 425 nm indicating HTA increased. In addition, as shown in FIG. 7B, it was confirmed that, as the contact time elapsed, the fluorescence intensity increased linearly ($y=1.614x+0.919$, $R^2=0.9807$). That is, as shown in FIG. 7C, it was confirmed that, as the contact time elapsed, the concentration of HTA increased linearly ($y=4.1969x-0.2106$, $R^2=0.9807$).

Example 5: Measurement of Only Hydrogen Peroxide as Gas to be Measured

As an OH radical detection probe, a solution in which 2 mmol/L of terephthalic acid was dissolved in DMF and methanol (volume ratio of 4:1) was used. In addition, hydrogen peroxide was used as a gas to be measured. In Example 5, heating was performed at 60° C. by the heating unit 120. Moreover, the OH radical detection probe after being brought into contact with hydrogen peroxide was irradiated with UV light, and the intensity of fluorescence generated from the OH radical detection probe was measured.

Figure 8A:
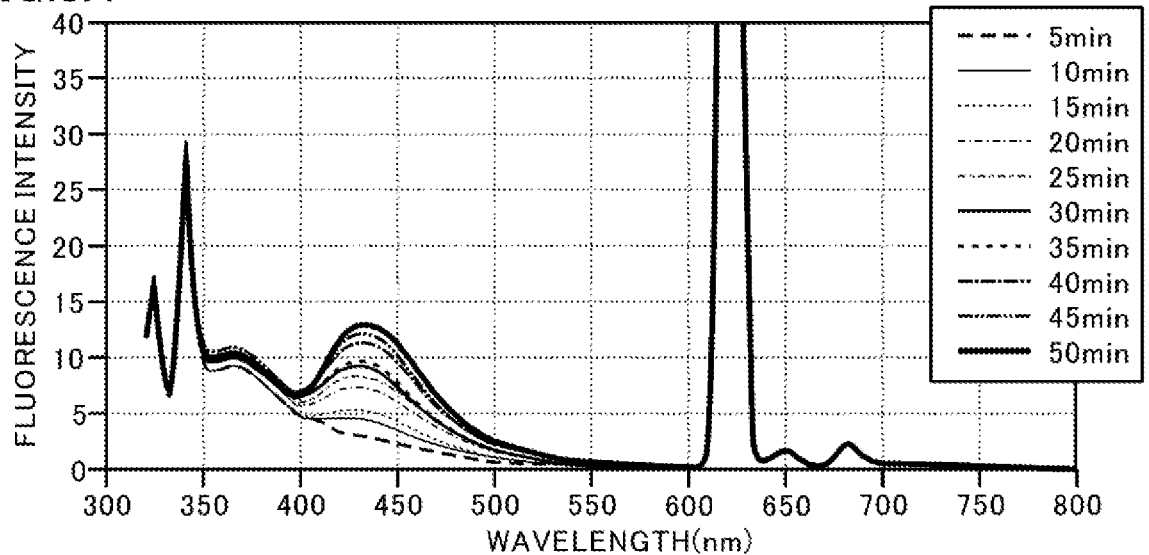
FIG. 8A is a graph for showing fluorescence spectra of Example 5.
Figure 8B:
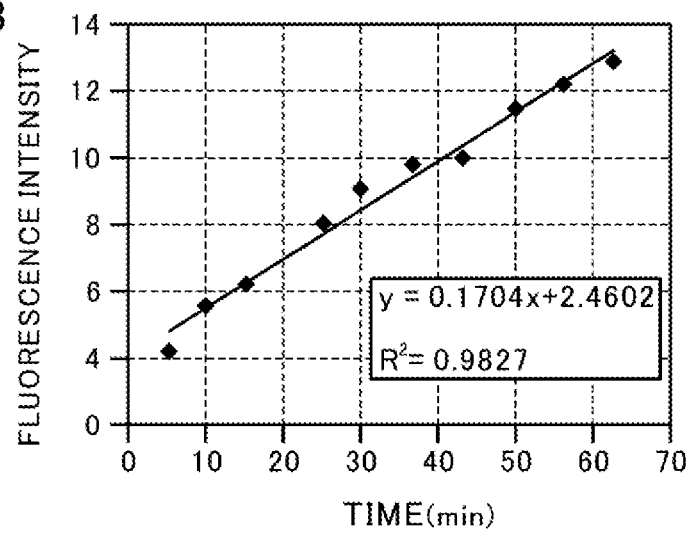
FIG. 8B is a graph for showing a relationship between: a contact time (min) of a gas to be measured and an OH radical detection probe; and a fluorescence intensity in Example 5.
Figure 8C:
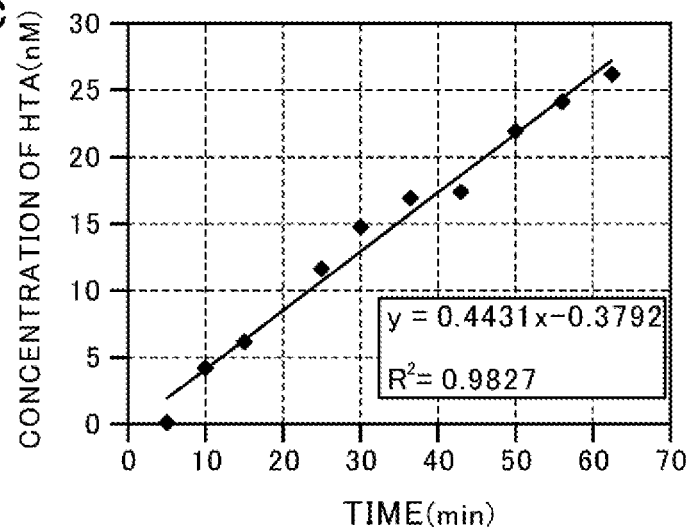
FIG. 8C is a graph for showing a relationship between: the contact time (min) of the gas to be measured and the OH radical detection probe; and a concentration (nM) of ETA in the OH radical detection probe in Example 5.

FIG. 8A to FIG. 8C are graphs for showing the results of Example 5. FIG. 8A is a graph for showing fluorescence spectra of Example 5. FIG. 8B is a graph for showing a relationship between: a contact time (min) of the gas to be measured and the OH radical detection probe; and the fluorescence intensity in Example 5. FIG. 8C is a graph for showing a relationship between: the contact time (min) of the gas to be measured and the OH radical detection probe; and the concentration (nM) of HTA in the OH radical detection probe in Example 5.

As shown in FIG. 8A and FIG. 8B, it was found that, as the contact time increased to 5 minutes, 10 minutes, 15 minutes, 20 minutes, 25 minutes, 30 minutes, 35 minutes, 40 minutes, 45 minutes, and 50 minutes, the intensity of fluorescence having a wavelength of 425 nm indicating HTA increased. In addition, as shown in FIG. 8B, it was confirmed that, as the contact time elapsed, the fluorescence intensity increased linearly (y=0.1704x+2.4602, $R^2$=0.9827). That is, as shown in FIG. 8C, was confirmed that, as the contact time elapsed, the concentration of HTA increased linearly (y=0.4431x−0.3792, $R^2$=0.9827).

Example 6: Measurement of Mixed Gas of Ozone and Hydrogen Peroxide as Gas to be Measured As an OH radical detection probe, a solution in which 2 mmol/L of terephthalic acid was dissolved in DMF and methanol (volume ratio of 4:1) was used. In addition, a mixed gas of ozone and hydrogen peroxide was used as a gas to be measured. In Example 6, heating was performed at 60° C. by the heating unit 120. Moreover, the OH radical detection probe after being brought into contact with the mixed gas of ozone and hydrogen peroxide was irradiated with UV light, and the intensity of fluorescence generated from the OH radical detection probe was measured.

Figure 9A:
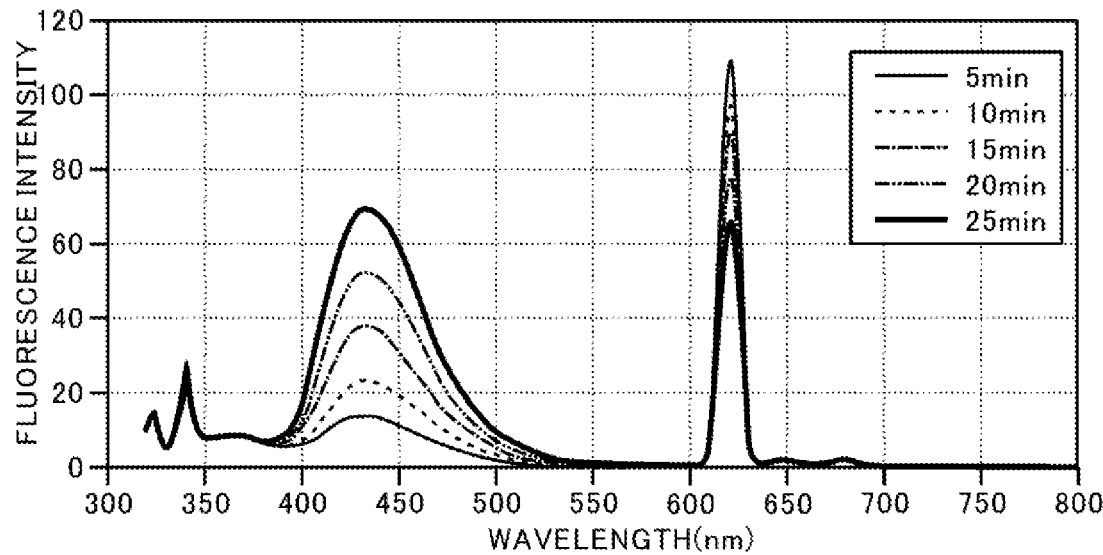
FIG. 9A is a graph for showing fluorescence spectra of Example 6.
Figure 9B:
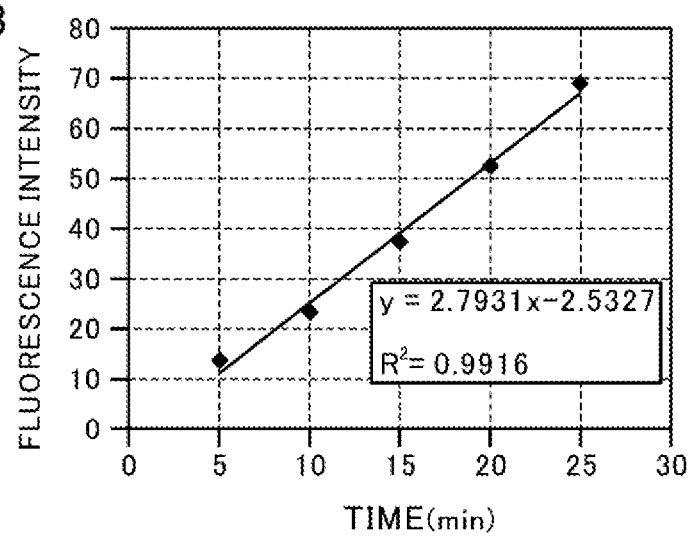
FIG. 9B is a graph for showing a relationship between: a contact time (min) of a gas to be measured and an OH radical detection probe; and a fluorescence intensity in Example 6.
Figure 9C:
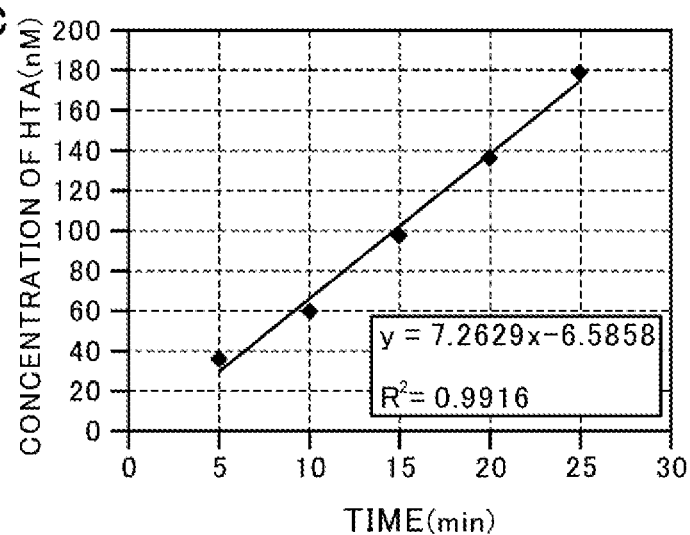
FIG. 9C is a graph for showing a relationship between: the contact time (min) of the gas to be measured and the OH radical detection probe; and a concentration (nM) of HTA in the OH radical detection probe in Example 6.

FIG. 9A to FIG. 9C are graphs for showing the results of Example 6. FIG. 9A is a graph for showing fluorescence spectra of Example 6. FIG. 9B is a graph for showing a relationship between: a contact time (min) of the gas to be measured and the OH radical detection probe; and the fluorescence intensity in Example 6. FIG. 9C is a graph for showing a relationship between: the contact time (min) of the gas to be measured and the OH radical detection probe; and the concentration (nM) of HTA in the OH radical detection probe in Example 6.

As shown in FIG. 9A and FIG. 9B, it was found that, as the contact time increased to 5 minutes, 10 minutes, 15 minutes, 20 minutes, and 25 minutes, the intensity of fluorescence having a wavelength of 425 nm indicating HTA increased. In addition, as shown in FIG. 9B, it was confirmed that, as the contact time elapsed, the fluorescence intensity increased linearly (y=2.7931x−2.5327, $R^2$=0.9916). That is, as shown in FIG. 9C, it was confirmed that, as the contact time elapsed, the concentration of HTA increased linearly (y=7.2629x−6.5858, $R^2$=0.9916).

Figure 10:
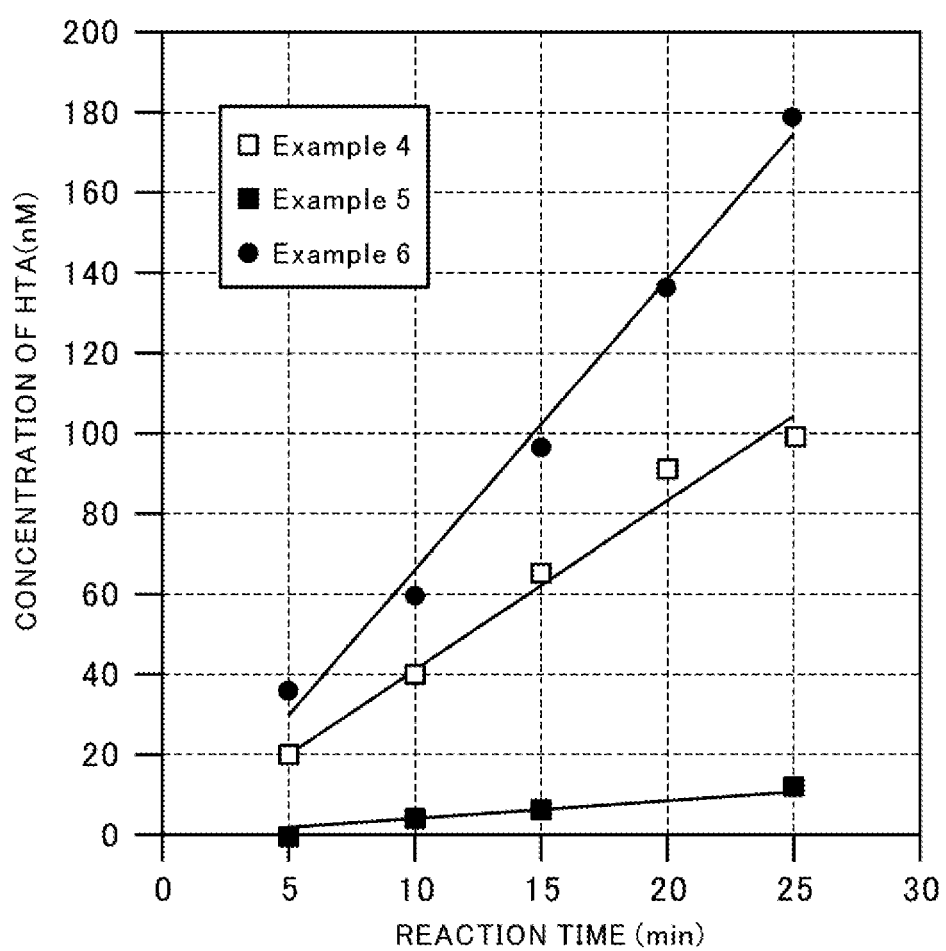
FIG. 10 is a graph for showing the concentration of HTA generated in each of the OH radical detection probes through use of the gases to be measured in Example 4 to Example 6.

FIG. 10 is a graph for showing the concentration of HTA generated in each of the OH radical detection probes through use of the gases to be measured in Example 4 to Example 6. In FIG. 10, Example 4 is represented by a white square, Example 5 is represented by a black square, and Example 6 is represented by a black circle. In Example 4 to Example 6, the concentration of HTA at a time when the reaction time (contact time of the OH radical detection probe 102 and the gas to be measured) was 5 minutes, 10 minutes, 15 minutes, 20 minutes, and 25 minutes was derived.

As a result, as shown in FIG. 10, in each of Example 4 to Example 6, it was found that, as the reaction time increased, the concentration of HTA (concentration of the OH radical) increased. In addition, it was found that the concentration of HTA in Example 6 (mixed gas of ozone and hydrogen peroxide) was higher than that in Example 4 (mixed gas of ozone and water vapor). It was found that the concentration of HTA in Example 4 was higher than that in Example 5 (only hydrogen peroxide).

Example 7: Case Using Methanol as Polar Protic Organic Solvent

A mixed gas of ozone and water vapor was measured through use of an OH radical detection probe in which 2 mmol/L of terephthalic acid was dissolved in DMF and methanol (volume ratio of 4:1), and the generation speed (nM/min) of HTA was determined based on the concentration of HTA.

Figure 11A:
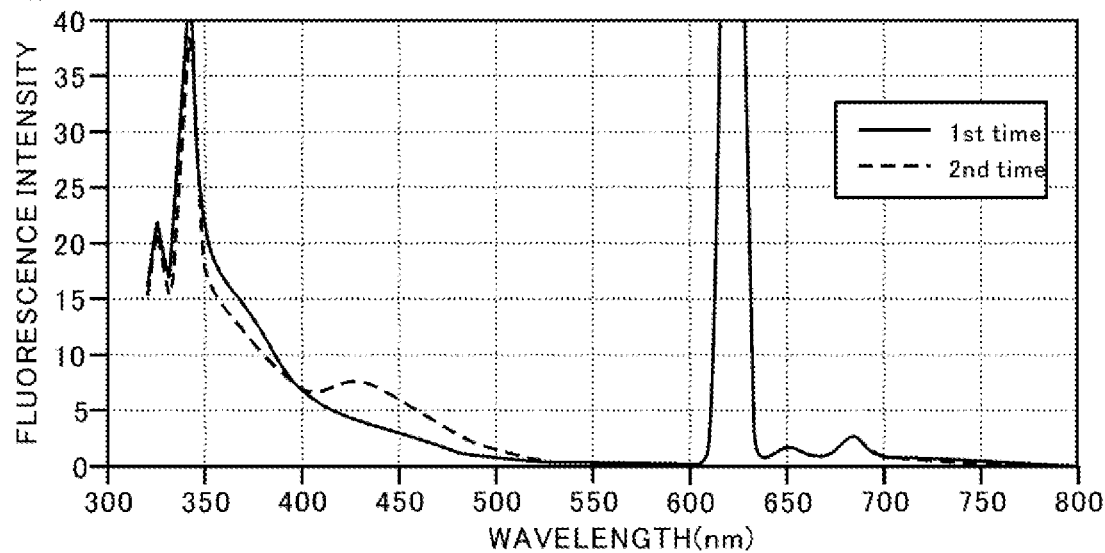
FIG. 11A is a graph for showing fluorescence spectra of Example 7.
Figure 11B:
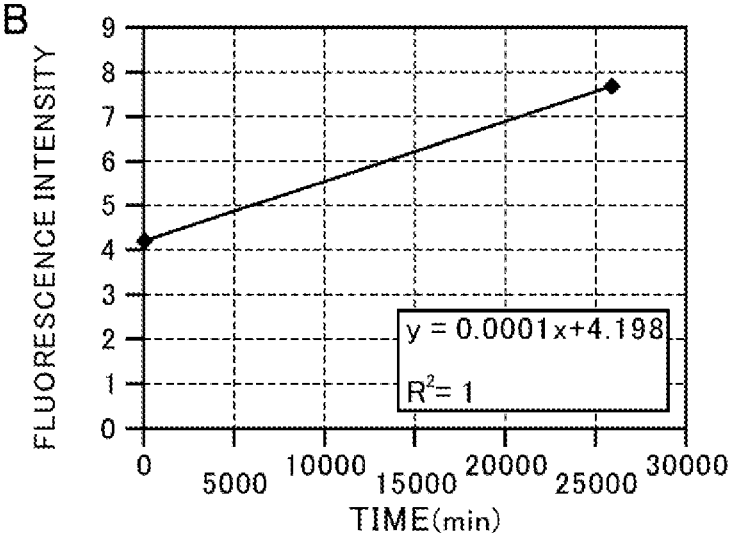
FIG. 11B is a graph for showing a relationship between: a contact time (min) of a gas to be measured and an OH radical detection probe; and a fluorescence intensity in Example 7.

FIG. 11A and FIG. 11B are graphs for showing the results of Example 7. FIG. 11A is a graph for showing fluorescence spectra of Example 7. FIG. 11B is a graph for showing a relationship between: a contact time (min) of the gas to be measured and the OH radical detection probe; and a fluorescence intensity in Example 7. In FIG. 11A, the second time represents a measurement result after 18 days (25,920 minutes) from the first time.

As shown in FIG. 11A and FIG. 11B, in the OH radical detection probe using methanol as the polar protic organic solvent, the generation speed of HTA was about 0.00034 nM/min.

Example 8: Case Using Ethanol as Polar Protic Organic Solvent

A mixed gas of ozone and water vapor was measured through use of an OH radical detection probe in which 2 mmol/L of terephthalic acid was dissolved in DMF and ethanol (volume ratio of 4:1), and the generation speed (nM/min) of HTA was determined based on the concentration of HTA.

Figure 12A:
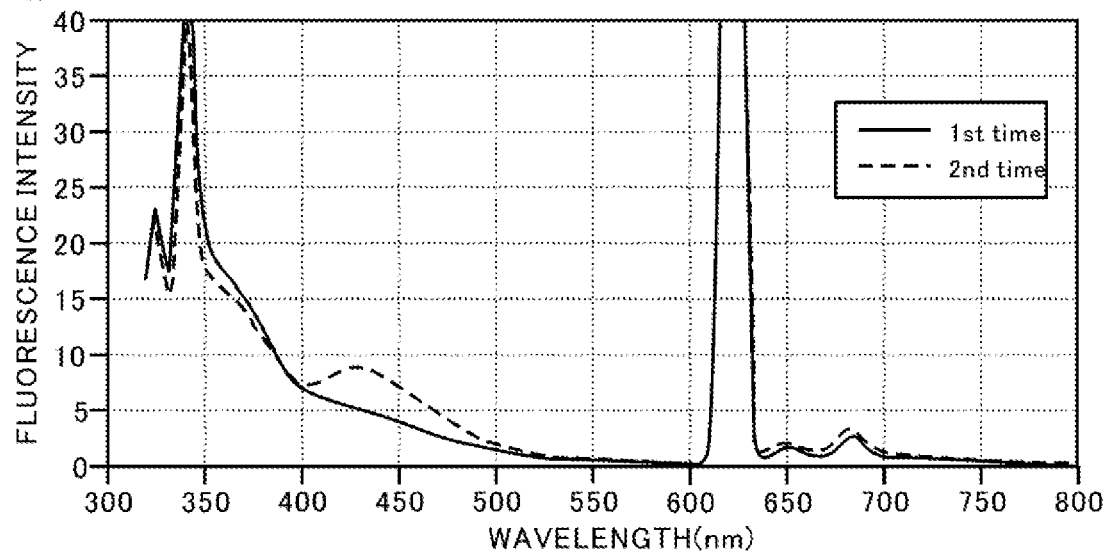
FIG. 12A is a graph for showing fluorescence spectra of Example 8.
Figure 12B:
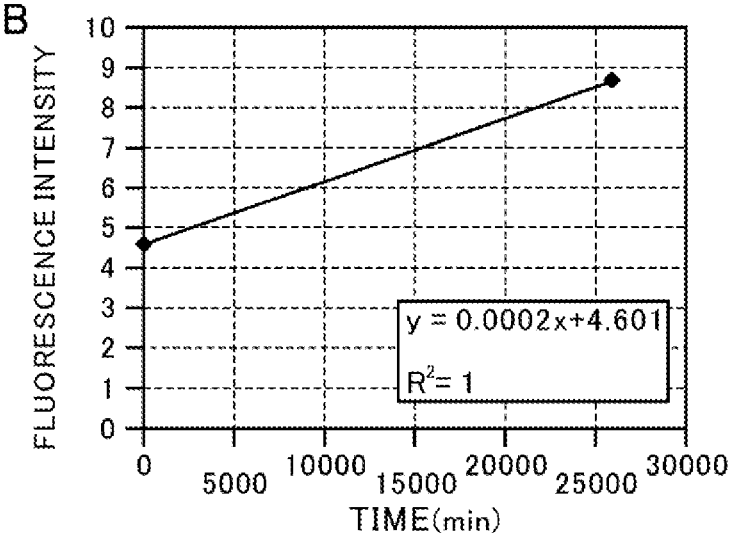
FIG. 12B is a graph for showing a relationship between: a contact time (min) of a gas to be measured and an OH radical detection probe; and a fluorescence intensity in Example 8.

FIG. 12A and FIG. 12B are graphs for showing the results of Example 8. FIG. 12A is a graph for showing fluorescence spectra of Example 8. FIG. 12B is a graph for showing a relationship between: a contact time (min) of the gas to be measured and the OH radical detection probe; and a fluorescence intensity in Example 8. In FIG. 12A, the second time represents a measurement result after 18 days (25,920 minutes) from the first time.

As shown in FIG. 12A and FIG. 12B, in the OH radical detection probe using ethanol as the polar protic organic solvent, the generation speed of HTA was about 0.00041 nM/min.

Example 9: Case Using 2-Propanol as Polar Protic Organic Solvent

A mixed gas of ozone and water vapor was measured through use of an OH radical detection probe in which 2 mmol/L of terephthalic acid was dissolved in DMF and 2-propanol (volume ratio of 4:1), and the generation speed (nM/min) of HTA was determined based on the concentration of HTA.

Figure 13A:
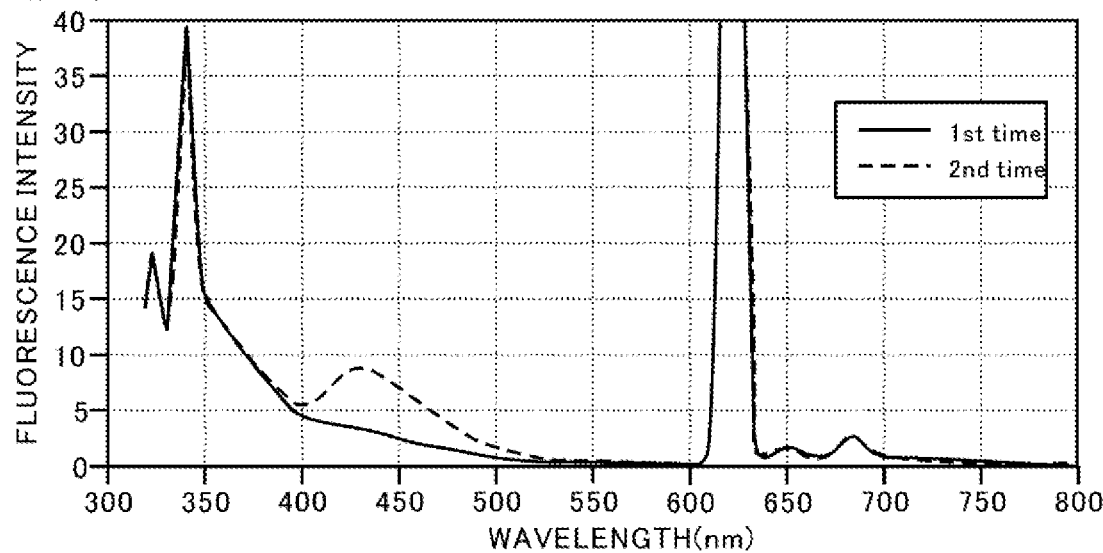
FIG. 13A is a graph for showing fluorescence spectra of Example 9.
Figure 13B:
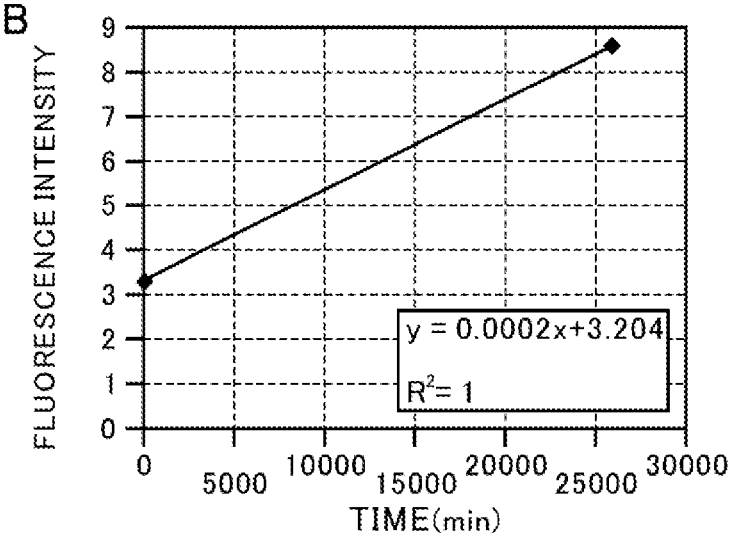
FIG. 13B is a graph for showing a relationship between: a contact time (min) of a gas to be measured and an OH radical detection probe; and a fluorescence intensity in Example 9.

FIG. 13A and FIG. 13B are graphs for showing the results of Example 9. FIG. 13A is a graph for showing fluorescence spectra of Example 9. FIG. 13B is a graph for showing a relationship between: a contact time (min) of the gas to be measured and the OH radical detection probe; and a fluorescence intensity in Example 9. In FIG. 13A, the second time represents a measurement result after 18 days (25,920 minutes) from the first time.

As shown in FIG. 13A and FIG. 13B, in the OH radical detection probe using 2-propanol as the polar protic organic solvent, the generation speed of HTA was about 0.00054 nM/min.

It was confirmed from the results of Example 7 to Example 9 that methanol, ethanol, and 2-propanol were able to be efficiently used as the polar protic organic solvent.

The embodiment of the present disclosure has been described above with reference to the attached drawings, but, needless to say, the present disclosure is not limited to the embodiment. It is apparent that those skilled in the art may arrive at various alternations and modifications within the scope of claims, and those examples are construed as naturally falling within the technical scope of the present disclosure.

For example, in the above-mentioned embodiment, the description has been made taking as an example the configuration in which the OH radical detection probe includes the aromatic carboxylic acid as an OH radical scavenger. However, the OH radical detection probe may include an OH radical scavenger other than the aromatic carboxylic acid.

In addition, in the above-mentioned embodiment, the description has been made taking as an example the case in which the OH radical detection probe includes only the aromatic carboxylic acid, the polar aprotic organic solvent, and the polar protic organic solvent. However, the OH radical detection probe is only required to be free of water, and the OH radical detection probe may include another solvent.

In addition, in the above-mentioned embodiment, the description has been made taking as an example the configuration in which the OH radical measurement device 100 includes the heating unit 120. However, the heating unit 120 is not an essential component.

In addition, in the above-mentioned embodiment, the description has been made taking as an example the case in which the concentration conversion unit 140 includes the irradiation unit 150, the measurement unit 160, and the control unit 170. However, there is no limitation on the configuration of the concentration conversion unit 140 as long as the concentration of an OH radical in the gas to be measured can be converted based on the concentration of a reaction product of the aromatic carboxylic acid and the OH radical in the OH radical detection probe after being brought into contact with the gas to be measured. The concentration conversion unit 140 may be, for example, any one or any two or more of a gas chromatograph (GC), a liquid chromatograph (LC), a mass spectrometer (MS), a gas chromatograph-mass spectrometer (GC-MS, GC-MS/MS), a liquid chromatograph-mass spectrometer (LC-MS, LC-MS/MS), and an infrared spectrometer (IR).

INDUSTRIAL APPLICABILITY

The present disclosure is applicable to an OH radical detection probe, an OH radical measurement device, and an OH radical measurement method.

REFERENCE SIGNS LIST

S110 contact step
S120 irradiation and measurement step
S130 derivation step
100 OH radical measurement device
102 OH radical detection probe
110 accommodation unit
120 heating unit
130 gas supply unit
140 concentration conversion unit
150 irradiation unit
160 measurement unit
172 concentration derivation unit

What is claimed is:

1. An OH radical measurement device, comprising:
   an accommodation unit accommodating an OH radical detection probe, which is a mixture including an aromatic carboxylic acid, a polar aprotic organic solvent, and a polar protic organic solvent;
   a gas supply unit configured to supply a gas to be measured into the accommodation unit; and
   a concentration conversion unit configured to convert a concentration of an OH radical in the gas to be measured by measuring a concentration of a reaction product of the aromatic carboxylic acid and the OH radical in the OH radical detection probe after being brought into contact with the gas to be measured.

2. The OH radical measurement device according to claim 1, wherein the concentration conversion unit comprises:
   an irradiation unit configured to irradiate the OH radical detection probe after being brought into contact with the gas to be measured with UV light;
   a measurement unit configured to measure an intensity of fluorescence generated from the OH radical detection probe; and
   a concentration derivation unit configured to derive a concentration of the OH radical in the gas to be measured based on the intensity of the fluorescence measured by the measurement unit.

3. The OH radical measurement device according to claim 2, further comprising a heating unit configured to heat the gas to be measured in the accommodation unit.

4. The OH radical measurement device according to claim 1, wherein the concentration conversion unit comprises any one or any two or more of a gas chromatograph, a liquid chromatograph, a mass spectrometer, a gas chromatograph-mass spectrometer, a liquid chromatograph-mass spectrometer, and an infrared spectrometer.

5. The OH radical measurement device according to claim 4, further comprising a heating unit configured to heat the gas to be measured in the accommodation unit.

6. The OH radical measurement device according to claim 1, further comprising a heating unit configured to heat the gas to be measured in the accommodation unit.

7. An OH radical measurement method, comprising measuring an OH radical in a gas phase through use of an OH radical detection probe, which is a mixture including an aromatic carboxylic acid, a polar aprotic organic solvent, and a polar protic organic solvent, by:
   bringing the OH radical detection probe into contact with a gas to be measured; and
   converting a concentration of an OH radical in the gas to be measured by measuring a concentration of a reaction product of the aromatic carboxylic acid and the OH radical in the OH radical detection probe after being brought into contact with the gas to be measured.

* * * * *